United States Patent [19]

Atwal et al.

[11] Patent Number: 5,401,758

[45] Date of Patent: Mar. 28, 1995

[54] PYRIDINYL CYANOGUANIDINE COMPOUNDS

[75] Inventors: Karnail S. Atwal, Newton, Pa.; Francis N. Ferrara, Martinsville, N.J.

[73] Assignee: Bristol-Myers Squibb Company, Princeton, N.J.

[21] Appl. No.: 134,352

[22] Filed: Oct. 7, 1993

[51] Int. Cl.$^6$ .................... C07D 213/02; A61K 31/44
[52] U.S. Cl. ..................... 514/353; 546/306
[58] Field of Search ......................... 546/306; 514/353

[56] References Cited

U.S. PATENT DOCUMENTS

| 4,988,723 | 1/1991 | Shiokawa et al. . | |
| 5,006,523 | 4/1991 | Atwal . | |
| 5,011,837 | 4/1991 | Atwal et al. . | |
| 5,061,813 | 10/1991 | Atwal . | |
| 5,132,311 | 7/1992 | Liang | 514/307 |
| 5,140,031 | 8/1992 | Atwal et al. . | |

FOREIGN PATENT DOCUMENTS

| 0205292 | 12/1986 | European Pat. Off. . |
| 0214818 | 3/1987 | European Pat. Off. . |
| 0274821 | 7/1988 | European Pat. Off. . |
| 0344747 | 12/1989 | European Pat. Off. . |
| 0359537 | 3/1990 | European Pat. Off. . |
| 0389861 | 10/1990 | European Pat. Off. . |
| 0412531 | 2/1991 | European Pat. Off. . |
| WO8707607 | 12/1987 | WIPO . |

OTHER PUBLICATIONS

H. J. Petersen et al., "Synthesis and Hypotensive Activity of N-Alkyl-N-cyano-N'", *J. of Med. Chem.*, vol. 21, No. 8, (Aug. 1978), pp. 773-781.

V. A. Ashwood et al., "Synthesis and Antihypertensive Activity of 4-(Cyclic amido)-2H-1-benzopyrans", *J. Med. Chem.*, (1986) 29, pp. 2194-2201.

C. R. Rasmussen et al., "Improved Procedures for the Preparation of Cycloalkyl-, Arylalkyl-, and Arylthioureas", *Synthesis*, (Jun. 1988), pp. 456-459.

V. V. Mozolis et al., "Preparation of N-Substituted Thiourea", *Russian Chem. Reviews*, 42(7), (1973), pp. 587-595.

J. M. Evans et al., "Synthesis and Antihypertensive Activity of Substituted trans-4-Amino-3,4-dihydro-2,-2-dimethyl-2H-1-benzopyran-3-ols", *J. Med. Chem.*, (1983), 26, pp. 1582-1589.

R. W. Lang et al., "Synthesis of Selectively Trifluoromethylated Pyridine Derivatives as Potential Antihypertensives", *Helvetica Chimica Acta*, (1988), vol. 71, pp. 596-601.

P. Sebok et al., "Selective synthesis of Analogues of the Natural Precocenes, Synthesis and Regioselective (–Alkylation of 6-Chloro-and 6-Tert-Butyl-7,-8-Dihyedroxy-2,2-Dimethyl-4-Chromanones", *Heterocycles*, (1988), 27, pp. 2595-2607.

P. Teixidor et al., "Improved Preparation of Precocene II, Unexpected Results in the Reduction of Alkoxy Substituted Acetophenones and 4-Chromanones with Sodium Borohydride", *Heterocycles*, (1988), 27, pp. 2459-2465.

A. Banerji et al., "Enolates of o-Hydroxyacetophenones: Novel Synthesis of 2,2-Dialkyl-4-Chromanones", *Tetrahedron Letters*, No. 38, 1979, pp. 3685-3686.

G. Ariamala et al., "A Simple Route for the Synthesis of 4-Chlorochromenes and Chroman-4-ones", *Tetrahedron Letters*, (1988), vol. 29, No. 28, pp. 3487-3488.

*Primary Examiner*—Warren C. Ivy
*Assistant Examiner*—Zinna N. Davis
*Attorney, Agent, or Firm*—Ellen K. Park

[57] ABSTRACT

Compounds having the formula

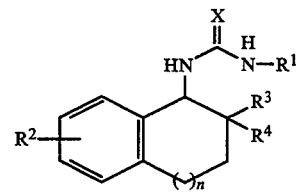

and pharmaceutically acceptable salts thereof wherein $R^1$ to $R^4$ and n are as defined herein and X is O, S or NCN. These compounds have potassium channel opening activity and are useful, therefore for example, as cardiovascular agents.

6 Claims, No Drawings

PYRIDINYL CYANOGUANIDINE COMPOUNDS

BRIEF DESCRIPTION OF THE INVENTION

The present invention is directed to compounds of the formula

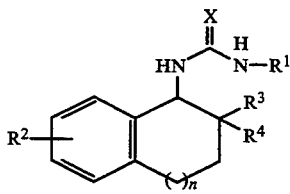

and pharmaceutically acceptable salts thereof. As used in formula I, and throughout the specification, the symbols have the following meanings:

X is O, S or NCN;

$R^1$ is aryl or heterocyclo;

$R^2$ is hydrogen, alkyl, haloalkyl, alkenyl, alkynyl, cycloalkyl, arylalkyl, (cycloalkyl)alkyl, —CN, —$NO_2$, —COR, —COOR, —CONHR, —$CONR^5$, —$CF_3$, —S—alkyl, —SOalkyl, —$SO_2$alkyl, halogen, amino, substituted amino, hydroxy, —O—alkyl, —$OCF_3$, —$OCH_2CF_3$, —OCOalkyl, —OCONRalkyl, —NRCOalkyl, —NRCOOalkyl or —$NRCONR^5$, where R is hydrogen, alkyl, haloalkyl, aryl, arylalkyl, cycloalkyl or (cycloalkyl)alkyl;

$R^3$ and $R^4$ are independently hydrogen, alkyl, aryl or arylalkyl; or $R^3$ and $R^4$ taken together with the carbon atom to which they are attached form a 3- to 7-membered carbocyclic ring;

$R^5$ is hydrogen, hydroxy or —OCOR; and n is 0 or the integer 1 or 2.

The compounds of this invention possess potassium channel opening activity and are useful, for example as cardiovascular agents.

DESCRIPTION OF THE INVENTION

The present invention provides for compounds of formula I, pharmaceutical compositions employing such compounds and for methods of using such compounds. Listed below are definitions of various terms used to describe the compounds of the instant invention. These definitions apply to the terms as they are used throughout the specification (unless they are otherwise limited in specific instances either individually or as part of a larger group.

The term "alkyl" refers to both straight and branched chain groups having 1 to 8 carbon atoms in the normal chain, preferably 1 to 5 carbons, such as methyl, ethyl, propyl, butyl, pentyl, hexyl, heptyl, octyl, the various branched chain isomers thereof, such as isopropyl, t-butyl, isobutyl, isohexyl, 4,4-dimethylpentyl, 2,2,4-trimethylpentyl and the like as well as such groups including a halo substituent such as $CCl_3$ or $CF_3$, an alkoxy substituent, an aryl substituent, an alkylaryl substituent, a haloaryl substituent, a cycloalkyl substituent, a (cycloalkyl)alkyl substituent, a hydroxy substituent, an alkylamino substituent, an alkanoylamino substituent, an arylcarbonylamino substituent, a nitro substituent, a cyano substituent, a thiol substituent or an alkylthio substituent.

The term "alkoxy" refers to any of the above alkyl groups linked to an oxygen atom.

The term "alkylthio" refers to any of the above alkyl groups linked to a sulfur atom.

The term "alkenyl" refers to any of the above alkyl groups further containing at least one carbon to carbon double bond.

The term "alkynyl" refers to any of the above alkyl groups further containing at least one carbon to carbon triple bond.

The term "cycloalkyl" refers to saturated cyclic hydrocarbon groups containing 3 to 7 ring carbons with cyclopropyl, cyclopentyl and cyclohexyl being preferred.

The term "halogen" or "halo" refers to chlorine, bromine, iodine and fluorine.

The term "aryl" refers to phenyl, 1-naphthyl, 2-naphthyl; phenyl, 1-naphthyl, 2-naphthyl, mono-substituted with ($C_1$-$C_4$)-alkyl, ($C_1$-$C_4$)-alkylthio, ($C_1$-$C_4$)-alkoxy, halo, nitro, cyano, hydroxy, amino, —NH—($C_1$-$C_4$)-alkyl, —N(($C_1$-$C_4$)-alkyl), —$CF_3$, —$OCHF_2$,

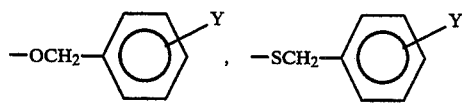

(wherein Y is hydrogen, ($C_1$-$C_4$)-alkyl, ($C_1$-$C_4$)-alkylthio, ($C_1$-$C_4$)-alkoxy, halo, hydroxy or —$CF_3$, —O—$CH_2$-cycloalkyl, or —S—$CH_2$-cycloalkyl; and phenyl, 1-naphthyl or 2-naphthyl, di-substituted with methyl, methoxy, methylthio, halo, —$CF_3$, nitro, amino or —$OCHF_2$. Preferred aryl groups include unsubstituted phenyl and monosubstituted phenyl wherein the substituents are ($C_1$-$C_4$)-alkyl, methoxy, halo, nitro, cyano or —$CF_3$.

The term "heterocyclo" or "hetero" refers to fully saturated or unsaturated rings of 5 or 6 atoms containing one or two oxygen and/or sulfur atoms and/or one to four nitrogen atoms provided that the total number of hetero atoms in the ring is four or less. The hetero ring is attached by way of an available atom. Preferred monocyclic hetero groups include 2- and 3-thienyl, 2- and 3-furyl, 2-, 3- and 4-pyridyl and imidazolyl. The term hetero also includes bicyclic rings wherein the five or six membered ring containing oxygen, sulfur and/or nitrogen atoms as defined above is fused to a benzene ring and the bicyclic ring is attached by way of an available carbon atom. Preferred bicyclic hetero groups include 4-, 5-, 6- or 7-indolyl, 4-, 5-, 6- or 7-isoindolyl, 5-, 6-, 7- or 8-quinolinyl, 5-, 6-, 7- or 8-isoquinolinyl, 4-, 5-, 6- or 7-benzothiazolyl, 4-, 5-, 6- or 7-benzoxazolyl, 4-, 5-, 6- or 7-benzimidazolyl, 4-, 5-, 6- or 7-benzoxadiazolyl and 4-, 5-, 6- or 7-benzofuranzanyl.

The term "heterocyclo" or "hetero" also includes such monocyclic and bicyclic rings wherein an available carbon atom is substituted with a ($C_1$-$C_4$)-alkyl, ($C_1$-$C_4$)-alkylthio, ($C_1$-$C_4$)-alkoxy, halo, nitro, keto, cyano, hydroxy, amino, —NH—($C_1$-$C_4$)-alkyl, —N(($C_1$-$C_4$)-alkyl)$_2$, —$CF_3$ or —$OCHF_2$ or such monocyclic and bicyclic rings wherein two or three available carbons have substituents selected from methyl, methoxy, methylthio, halo, —$CF_3$, nitro, hydroxy, amino and —$OCHF_2$.

The term "substituted amino" refers to a group of the formula —$NZ^1Z^2$ wherein $Z^1$ is hydrogen, alkyl, cycloalkyl, aryl, arylalkyl, (cycloalkyl)alkyl and $Z^2$ is alkyl, cycloalkyl, aryl, arylalkyl, (cycloalkyl)alkyl or $Z^1$ and $Z^2$ taken together with the nitrogen atom to which they are attached are 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, substituted with alkyl, alkoxy, alkylthio, halo, trifluoromethyl or hydroxy.

The compounds of formula I can be present as salts, in particular pharmaceutically acceptable salts. If the compounds of formula I have, for example, at least one basic center, they can form acid addition salts. These are formed, for example, with strong inorganic acids, such as mineral acids for example sulfuric acid, phosphoric acid or a hydrohalic acid, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, for example aspartic or glutamic acid, or such as benzoic acid, or with organic sulfonic acids, such as ($C_1$–$C_4$)-alkyl- or aryl-sulfonic acids which are unsubstituted or substituted, for example by halogen, for example methane- or p-toluene-sulfonic acid. Corresponding acid addition salts can also be formed having, if desired, an additionally present basic center. The compounds of formula I having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono-, di- or tri-lower alkylamine, for example ethyl-, tert-butyl-, diethyl-, diisopropyl-, triethyl-, tributyl- or dimethylpropylamine, or a mono-, di- or trihydroxy lower alkylamine, for example mono-, di- or triethanolamine. Corresponding internal salts may furthermore be formed. Salts which are unsuitable for pharmaceutical uses but which can be employed, for example, for the isolation or purification of free compounds I or their pharmaceutically acceptable salts, are also included.

All stereoisomers of the compounds of the instant invention are contemplated, either in admixture or in pure or substantially pure form. The compounds of the present invention can have asymmetric centers at any of the carbon atoms including any one of the R substituents. Consequently, compounds of formula I can exist in diastereomeric forms or in mixtures thereof. The above described processes can utilize racemates, enantiomers or diastereomers as starting materials. When diastereomeric products are prepared, they can be separated by conventional methods for example, chromatographic or fractional crystallization. Preferred compounds are those with the 3S or 4R stereochemistry.

It should be understood that the present invention includes prodrug forms of the compounds of formula I such as alkylesters of acids.

The compounds of the instant invention may, for example, be in the free or hydrate form, and may be obtained by methods exemplified by the following descriptions.

Compounds of formula I wherein X is NCN, $R^1$ is 3-pyridyl, $R^2$ is —CN, $R^3$ and $R^4$ are each methyl groups and n is 0, can be prepared according to the Scheme outlined below.

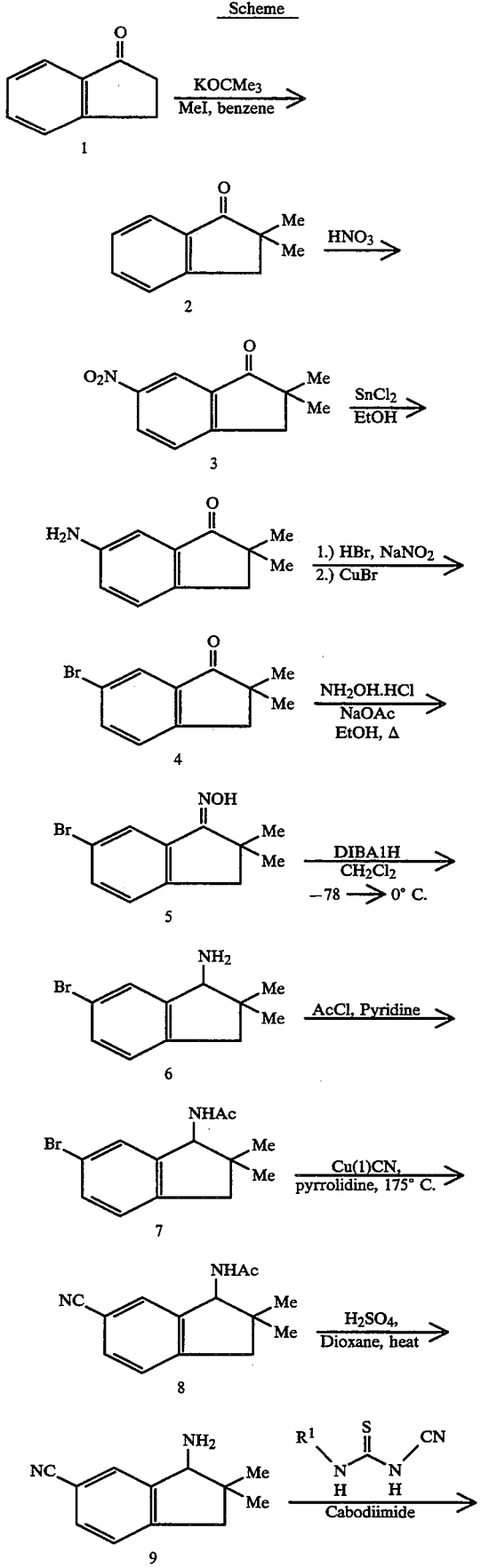

-continued
Scheme

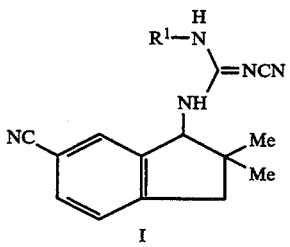

The indanone 1 is alkylated with an alkyl halide and a base such as potassium tert-butoxide to give compound 2 which upon nitration (fuming nitric acid) provides 3. The amino compound is converted to the bromide 4 via its diazonium salt, prepared by treatment with sodium nitrite and hydrobromic acid. The ketone 4 is convened its oxime 5 under standard conditions (hydroxyl amine hydrochloride and sodium acetate). The oxime 5 is reduced with diisobutylaluminum hydride in an organic solvent such as tetrahydrofuran, diethyl ether) to provide the amine 6. The amine 6 was protected and the resulting acetate 7 was heated with Cu(1)CN to give the cyano compound 8. The acetate was removed under acidic conditions and the amine 9 was convened to the desired product by treatment with the appropriate thiourea and in the presence of a carbodiimide. The bromide in the intermediate 7 can also be replaced with other groups such as trifluoromethyl, O-alkyl, S-alkyl, alkenyl, alkynyl etc., by methods described in the literature. Compounds wherein $R^2$ is other than nitrile and $R^3$ and $R^4$ are other than methyl groups can be prepared by appropriate modification of the above scheme.

Compounds of formula I wherein X is O or S and n is 0, can be prepared by treatment of a compound of formula 9 with an isocyanate or isothiocyanate of formula II $$R^1N=C=X$$

wherein X is O or S.

Compounds of formula II are commercially available or can be prepared by methods known in the literature.

Compounds of this invention wherein X is NCN can exist in tautomeric forms I', I" and I"'. All forms are included in the scope of this invention.

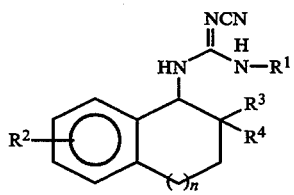

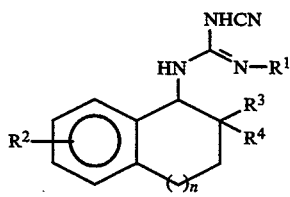

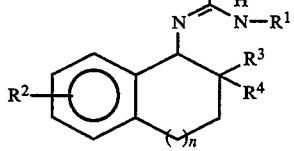

The preferred compounds of the present invention are those compounds of formula I where:
X is NCN;
$R^1$ is aryl or heterocyclo;
$R^2$ is hydrogen, cyano or halo;
$R^3$ and $R^4$ are methyl groups; and
n is zero.

Compounds of formula I may be used as antiischemic agents, i.e., for the treatment of hypertension and ischemic conditions such as myocardial ischemia, cerebral ischemia, lower limb ischemia and the like.

Thus a composition containing one (or a combination) of the compounds of this invention, may be administered to a species of mammal (e.g., humans) suffering from an ischemic or hypertensive condition.

A single dose, or two to four divided daily doses, provided on a basis of about 0.001 to about 100 mg per kilogram of body weight per day, preferably about 0.1 to about 25 mg per kilogram of body weight per day is appropriate. The substance is preferably administered orally, but parenteral routes such as the subcutaneous, intramuscular, intravenous or intraperitoneal routes or any other suitable delivery system, such as intranasal or transdermal routes can also be employed.

As a result of the potassium channel activating activity of compounds of this invention, these compounds are also useful in the treatment of cardiovascular disorders and any disorders associated with smooth muscle contraction. For example, compounds of the present invention are useful as therapy for congestive heart failure, therapy for peripheral vascular disorders (e.g. Raynaud's Disease), therapy for pulmonary hypertension, as anti-anginal agents, as antifibrillatory agents, and in limiting myocardial infarction.

Compounds of the present invention are additionally expected to be useful in the treatment of central nervous system disorders (e.g., Parkinsonism, as anti-tremor agents, epilepsy), in therapy for renal failure, in therapy for urinary incontinence, as anti-diarrheal agents, in therapy for pre-eclampsia, dysmenorrhea and premature labor, for the treatment of male impotence, as well as for the promotion of hair growth (e.g., in the treatment of male pattern baldness) and as anti-asthmatic agents.

The compounds of this invention can also be formulated in combination with a diuretic such as chlorothiazide, hydrochlorothiazide, flumethiazide, hydroflumethiazide, benzoflumethiazide, methylchlorothiazide, trichloromethiazide, polythiazide or benzthiazide as well as ethacrynic acid tricrynafen, chlorthalidone, furosemide, musolimine, bumetanide, triamterene, amiloride and spironolactone and salts of such compounds, angiotensin converting enzyme inhibitors such as captopril, zofenopril, fosinopril, enalapril, ceranopril, cilazopril, delapril, pentopril, quinapril, ramipril, lisinopril, and salts of such compounds, thrombolytic agents such as tissue plasminogen activator (tPA), recombinant tPA, streptokinase, urokinase, prourokinase, and anisoylated plasminogen streptokinase activator complex (APSAC, Eminase, Beecham Laboratories), or calcium channel blocking agents such as nifedipine or diltiazem. Such combination products if formulated as a fixed dose employ the compounds of this invention within the dose range described above and the other pharmaceutically active agent within its approved dose range.

The compounds of formula I, and combinations thereof, can be formulated, as described above, in compositions such as tablets, capsules or elixirs for oral administration, in sterile solutions or suspensions for parenteral administration, and may also be administered via transdermal patch or nasal inhalation solutions. About 10 to about 500 milligrams of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the rang indicated is obtained.

The following examples and preparations describe the manner and process of making and using the invention and are illustrative rather than limiting. It should be understood that there may be other embodiments which fall within the spirit and scope of the invention as defined by the claims appended hereto.

EXAMPLE

N″-Cyano-N′-(6-cyano-2,3-dihydro-2,2-dimethyl-1H-inden-1-yl)-N-(3-pyridinyl)guanidine

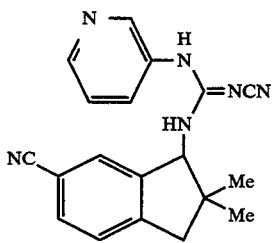

A. 2,3-Dihydro-2,2-dimethyindan-1-one

To a solution of 1-indanone (30 g, 0.23 mol) in dry benzene (350 mL) at room temperature under argon was added solid potassium-ter-butoxide (95%, 68 g, 0.58 mol). Methyl iodide (65.3 g, 0.46 mol) was added to the deep purple slurry with cooling over one hour. The reaction mixture was heated at reflux for two hours and poured over ice containing concentrated HCl solution (90 mL). Diethyl ether was added and the organic phase was separated. The aqueous phase was extracted with diethyl ether. The combined organic layers were washed with 5% sodium carbonate solution followed by saturated sodium chloride solution. The extracts were dried over magnesium sulfate and evaporated in vacuo to obtain 40 g of a dark brown oil. The oil was dissolved in ethyl acetate, treated with activated charcoal, and filtered through a pad of celite and silica gel. The filtrate was concentrated to obtain an orange solid which was triturated with cold pentane to afford the title compound (24.3 g, 66%) as a yellow solid, mp 44°-45° C. Analysis calculated for $C_{11}H_{12}O$: C, 82.46; H, 7.55. Found: C, 82.47; H, 7.53.

B. 2,3-Dihydro-2,2-dimethyl-6-nitroindan-1-one

A solution of urea (0.40 g) in nitric acid (90% fuming, 80 mL) was purged with air for twenty minutes, then cooled to −5° C. To this solution was added the title A compound (20.0 g, 0.12 mol) in portions while maintaining the reaction temperature <5° C. The reaction mixture was stirred at −5° to 5° C. for two hours and poured over ice. The aqueous mixture was extracted with ethyl acetate. The extracts were washed with saturated sodium bicarbonate solution, saturated sodium chloride solution, and dried over magnesium sulfate. The solvent was recovered under vacuum to obtain an orange solid which was crystallized from methanol to obtain the title compound (18.0 g, 73%) as a yellow crystalline solid, mp 103°-105° C. Analysis calculated for $C_{11}H_{11}NO_3$: C, 64.38; H, 5.40; N, 6.83. Found: C, 64.42; H, 5.38; N, 7.00.

C. 6-Amino-2,3-dihydro-2,2-dimethylindan-1-one

To a solution of the title B compound (10.0 g, 48.7 mmol) in ethanol (100 mL) was added stannous chloride dihydrate (54.9 g, 0.24 mol). The mixture was heated at 75° C. for one hour. The reaction mixture was poured over ice and neutralized by the addition of solid sodium bicarbonate. The pH was adjusted to 11-12 with 10N sodium hydroxide solution and the reaction mass was extracted with ethyl acetate. The extracts were washed with saturated sodium chloride solution, dried over magnesium sulfate and evaporated in vacuo to obtain the title compound (8.19 g, 96%) as a tan solid, mp 92°-94° C. The compound was used in the next step without further purification. Analysis calculated for $C_{11}H_{13}NO$: C, 75.40; H, 7.48; N, 7.99. Found: C, 75.30; H, 7.57; N, 7.99.

D. 6-Bromo-2,3-dihydro-2,2-dimethylindan-1-one

To a solution of the title C compound (21.48 g, 71.2 mmol) in ethanol (65 mL) cooled to 0° C. was added 48% aqueous hydrobromic acid (20 mL) followed by sodium nitrite solution (4.91 g dissolved in 8.8 mL of water) until a positive starch/iodide test result was obtained. The cold diazonium salt solution was added directly via pipette to a refluxing mixture of copper(1) bromide (11.23 g, 78.3 mmol) and 48% aqueous hydrobromic acid (20 mL). The reaction mixture was refluxed an additional 15 minutes upon completion of the addition, cooled to room temperature, and partitioned between ethyl acetate and 2N HCl. The organic phase was washed with 2N hydrochloric acid, saturated sodium bicarbonate solution, saturated sodium chloride solution, and dried over magnesium sulfate. The solvent was recovered under vacuum to obtain an orange solid which was triturated with cold pentane to obtain the title compound (13.17 g, 77%) as a pale yellow solid, mp 43°-45° C. Analysis calculated for $C_{11}H_{11}BrO$: C, 55.26; H, 4.64; Br, 33.42. Found: C, 55.38; H, 4.64; Br, 32.79.

E. 6-Bromo-2,3-dihydro-2,2-dimethylindan-1-one oxime

A mixture of the title D compound (11.64 g, 48.67 mmol), hydroxylamine hydrochloride (6.76 g, 97.3 mmol) and sodium acetate (7.19 g, 87.6 mmol) in ethanol (230 mL) was heated at reflux for 36 hours. The ethanol was recovered under vacuum and the residue was partitioned between water and ethyl acetate. The organic fraction was washed with 1N sodium hydroxide solution, saturated sodium chloride solution, dried over magnesium sulfate and evaporated in vacuo to obtain 12.27 g (99%) of an off-white solid as a 2.9:1 mixture of syn and anti oximes. The isomer mixture was chromatographed on silica eluting with 7.5% ethyl acetate in hexane to afford 8.94 g of the title product (syn isomer) as a white solid, mp 168°–170° C.

F. 6-Bromo-2,3-dihydro-2,2-dimethy-1H-inden-1-amine

To a solution of the title E compound (5.0 g, 19.7 mmol) in methylene chloride (200 mL) at 0° C. was added diisobutylaluminum hydride solution (1M in hexane, 5 eq., 147 mL) dropwise with stirring. The reaction mixture was stirred at 0° C. for 18 hours after which time it was diluted with methylene chloride (400 mL) and quenched by the addition of sodium fluoride (24.8 g) followed by water (8 mL). The solids were filtered and the filtrate was evaporated under vacuum to obtain an off-white solid (5.0 g). The crude material was chromatographed on silica gel eluting with hexane/ethyl acetate (9:1) to obtain 7-bromo-3,3-dimethyl-1,2,3,4-tetrahydro-1-quinoline (2.26 g, 48%) and the title compound (188 mg, 4%) as an oil.

G. 1-(Acetylamino)-6-bromo-2,3-dihydro-2,2-dimethyl-1H-indene

To a solution of the title F compound (0.57 g, 2.37 mmol) and pyridine (0.37 g) in dichloromethane (6 mL) at 0° C. was added acetyl chloride (0.20 g, 2.61 mmol) dropwise over 5 minutes. The solution was stirred at room temperature for one hour. The reaction mixture was partitioned between 1N hydrochloric acid solution and ethyl acetate. The organic phase was washed with saturated sodium bicarbonate solution followed by brine. The extracts were dried over magnesium sulfate and evaporated in vacuo to obtain the title compound (0.59 g, 88%) as a white solid.

H. 1-(Acetylamino)-2,3-dihydro-2,2-dimethyl-1H-indene-6-carbonitrile

A solution of the title G compound (0.68 g, 2.41 mmol) and copper(1)cyanide (0.45 g) in N-methylpyrrolidone (15 mL) under argon was heated at 175° C. for eight hours. The reaction mixture was cooled to room temperature, diluted with ethyl acetate, and filtered through a pad of celite. The filtrate was washed with distilled water, 1N hydrochloric acid solution and brine. The crude product solution was treated with activated charcoal, dried over magnesium sulfate and evaporated in vacuo to obtain the title compound (0.31 g, 56%) as a yellow gum which slowly solidified.

I. 1-Amino-2,3-dihydro-2,2-dimethyl-1H-indene-6-carbonitrile

A solution of the title H compound (0.31 g, 1.36 mmol) in a mixture of dioxane (4 mL) and 2.5N sulfuric acid solution (3.6 mL) was heated at 80° C. for four days. The reaction mixture was diluted with distilled water and extracted with ethyl acetate (discarded). The aqueous product solution was made basic (pH 12–14) with solid sodium hydroxide and extracted with diethyl ether. The ether extracts were washed with brine, dried over sodium sulfate and evaporated in vacuo to obtain the title compound (0.18 g, 68%) as a colorless gum.

J. N''-Cyano-N'-(6-cyano-2,3-dihydro-2,2-dimethyl-1H-inden-1-yl)-N-(3-pyridinyl)guanidine To a solution of the title I compound (0.18 g, 0.96 mmol) in N,N-dimethylformamide (1.25 mL) was added N-cyano-N'-3-pyridinylthiourea, monosodium salt (0.25 g, 1.24 mmol, prepared by the treatment of 3-pyridyl isothiocyanate with mono sodium cyanamide) and 1-(3-dimethylaminopropyl)-2-ethylcarbodiimide hydrochloride (0.24 g, 1.24 mmol). The reaction mixture was stirred at room temperature for 24 hours and partitioned between ethyl acetate and water. The organic phase was washed with distilled water, brine, dried over magnesium sulfate and evaporated to obtain a yellow foam. The crude material was purified by crystallization from isopropyl ether/ethyl acetate/hexane to obtain the title compound (100 mg, 31%) as an off-white solid, mp 224°–225° C. Analysis calculated for $C_{19}H_{18}N_6 \cdot 0.09H_2O \cdot 0.08$ isopropyl ether: C, 68.78; H, 5.72; N, 24.70. Found: C, 68.73; H, 5.38; N, 24.65

What is claimed is:

1. A compound of the formula

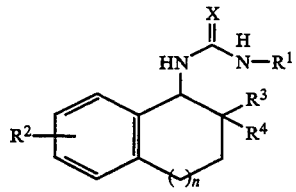

or pharmaceutically acceptable salts thereof wherein
X is O, S or NCN;
$R^1$ is pyridinyl;
$R^2$ is hydrogen, alkyl, haloalkyl, alkenyl, alkynyl, cycloalkyl, arylalkyl, (cycloalkyl)alkyl, —CN, —NO$_2$, —COR, —COOR, —CONHR, —CONR$^5$, —CF$_3$, —S—alkyl, —SOalkyl, —SO$_2$alkyl, halogen, amino, substituted amino, hydroxy, —O—alkyl, —OCF$_3$, —OCH$_2$CF$_3$, —OCOalkyl, —O-CONRalkyl, —NRCOalkyl, —NRCOOalkyl or —NRCONR$^5$, where R is hydrogen, alkyl, haloalkyl, aryl, arylalkyl, cycloalkyl or (cycloalkyl)alkyl;
$R^3$ and $R^4$ are independently hydrogen, alkyl, aryl or arylalkyl; or $R^3$ and $R^4$ taken together with the carbon atom to which they are attached form a 3- to 7-membered carbocyclic ring;
$R^5$ is hydrogen, hydroxy or —OCOR; and
n is 0 or the integer 1 or 2.

2. A compound as recited in claim 1 wherein
X is NCN;
$R^2$ is hydrogen, cyano or halo;
$R^3$ and $R^4$ are methyl groups; and
n is zero.

3. The compound as recited in claim 1, which is N''-cyano-N'-(6-cyano-2,3-dihydro-2,2-dimethyl-1H-inden-1-yl)-N-(3-pyridinyl)guanidine or a pharmaceutically acceptable salt thereof.

4. A pharmaceutical composition comprising a compound of claim 1 and a pharmaceutically acceptable carrier.

5. A method for treating ischemia comprising administering to a mammalian specie in need thereof a therapeutically effective amount of a composition of claim 4.

6. A method for treating hypertension comprising administering to a mammalian specie in need thereof a therapeutically effective amount of a composition of claim 4.

* * * * *